US00PP34277P2

(12) United States Plant Patent
Mekada et al.

(10) Patent No.: US PP34,277 P2
(45) Date of Patent: May 31, 2022

(54) ***HYDRANGEA* PLANT NAMED 'CMT 010'**

(50) Latin Name: ***Hydrangea macrophylla* X *Hydrangea hybrida***
Varietal Denomination: CMT 010

(71) Applicants: Hiroyuki Mekada, Shimane (JP); Hiroko Inamura, Shimane (JP); Tetsuya Kako, Shimane (JP); Yuka Shimizu, Shimane (JP)

(72) Inventors: Hiroyuki Mekada, Shimane (JP); Hiroko Inamura, Shimane (JP); Tetsuya Kako, Shimane (JP); Yuka Shimizu, Shimane (JP)

(73) Assignee: SHIMANE PREFECTURE, Matsue (JP)

( * ) Notice: Subject to any disclaimer, the term of this patent is extended or adjusted under 35 U.S.C. 154(b) by 0 days.

(21) Appl. No.: 17/506,171

(22) Filed: Oct. 20, 2021

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

PUBLICATIONS

CPVO Register. https://online.plantvarieties.eu/public-ConsultationDetails?registerId=20203424&denomination=CMT%20010. 2 pages. (Year: 2021).*

* cited by examiner

*Primary Examiner* — Karen M Redden
(74) *Attorney, Agent, or Firm* — C. Anne Whealy

(57) ABSTRACT

A new and distinct cultivar of *Hydrangea* plant named 'CMT 010', characterized by its relatively compact and uniformly mounding plant habit; freely branching habit; strong and sturdy stems; freely flowering habit; large and dense intermediate lacecap-type inflorescences with numerous double-type sterile flowers that are white in color; and good post-production longevity.

1 Drawing Sheet

Figure 1:
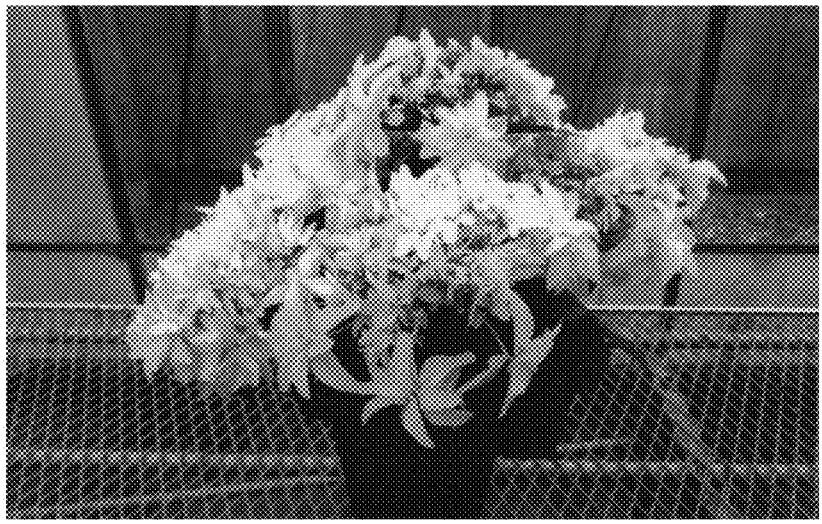

Botanical designation: *Hydrangea macrophylla* X *Hydrangea hybrida.*

Cultivar denomination: 'CMT 010'.

STATEMENT REGARDING PRIOR DISCLOSURES BY INVENTOR/APPLICANT

A Japanese Plant Breeder's Rights application for the instant plant was filed by the Assignee, Shimane Prefecture of Shimane, Japan on Jun. 22, 2020, application number 34776. Foreign priority is not claimed to this application.

The Inventors/Applicants and Assignee assert that no publications nor advertisements relating to sales, offers for sale or public distribution occurred more than one year prior to the effective filing date of this application. Any information about the claimed plant would have been obtained from a direct or indirect disclosure from the Inventors/Applicants and/or the Assignee. Inventors/Applicants and Assignee claim a prior art exception under 35 U.S.C. 102(b)(1) for sales prior to the filing date but less than one year prior to the effective filing date.

BACKGROUND OF THE INVENTION

The present invention relates to a new and distinct cultivar of *Hydrangea* plant, botanically known as *Hydrangea macrophylla* X *Hydrangea hybrida*, commercially referred to as an intermediate lacecap-type *Hydrangea* and hereinafter referred to by the name 'CMT 010'.

The new *Hydrangea* plant is a product of a planned breeding program conducted by the Inventors in Izumo-shi, Shimane, Japan. The objective of the breeding program is to create new freely-branching and early flowering *Hydrangea* plants with compact plant habit and intermediate lacecap-type inflorescences.

The new *Hydrangea* plant originated from a self-pollination made by the Inventors in June, 2009 in Izumo-shi, Shimane, Japan, of a proprietary selection of *Hydrangea macrophylla* X *Hydrangea hybrida* identified as code number Cmt005-014, not patented. The new *Hydrangea* plant was discovered and selected by the Inventors as a single flowering plant from within the progeny of the stated self-pollination in a controlled greenhouse environment in Izumo-shi, Shimane, Japan in April, 2012.

Asexual reproduction of the new *Hydrangea* plant by vegetative tip cuttings in a controlled environment in Izumo-shi, Shimane, Japan since January, 2015 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'CMT 010'. These characteristics in combination distinguish 'CMT 010' as a new and distinct *Hydrangea* plant:

1. Relatively compact and uniformly mounding plant habit.
2. Freely branching habit.
3. Strong and sturdy stems.
4. Freely flowering habit.
5. Large and dense intermediate lacecap-type inflorescences with numerous double-type sterile flowers that are white in color.
6. Good post-production longevity.

Plants of the new *Hydrangea* can be compared to plants of the parent selection. Plants of the new *Hydrangea* differ primarily from plants of the parent selection in inflorescence and flower form. Plants of the new *Hydrangea* have intermediate lacecap-type inflorescences with double-type sterile flowers whereas plants of the parent selection have lacecap inflorescences with single-type sterile flowers.

Plants of the new *Hydrangea* can be compared to plants of the *Hydrangea macrophylla* 'FRCK 003 S 123', disclosed in a U.S. Plant patent application Ser. No. 17/506,251 filed concurrently. In side-by-side comparisons, plants of the new *Hydrangea* differ primarily from plants of 'FRCK 003 S 123' in the following characteristics:

1. Plants of the new *Hydrangea* have darker green-colored leaves than plants of 'FRCK 003 S 123'.
2. Sterile flowers of plants of the new *Hydrangea* have lanceolate-shaped sepals with entire margins whereas sterile flowers of plants of 'FRCK 003 S 123' have broadly ovate-shape sepals with serrate margins.
3. Sterile flowers of plants of the new *Hydrangea* are white in color whereas sterile flowers of plants of 'FRCK 003 S 123' are violet blue and white bi-colored when "blued".
4. Flower pedicels of plants of the new *Hydrangea* are more upright than and not as horizontal as flower pedicels of plants of 'FRCK 003 S 123'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph at the top of the sheet (FIG. 1) is a side perspective view of a typical flowering plant of 'CMT 010' grown in a container.

Figure 2:
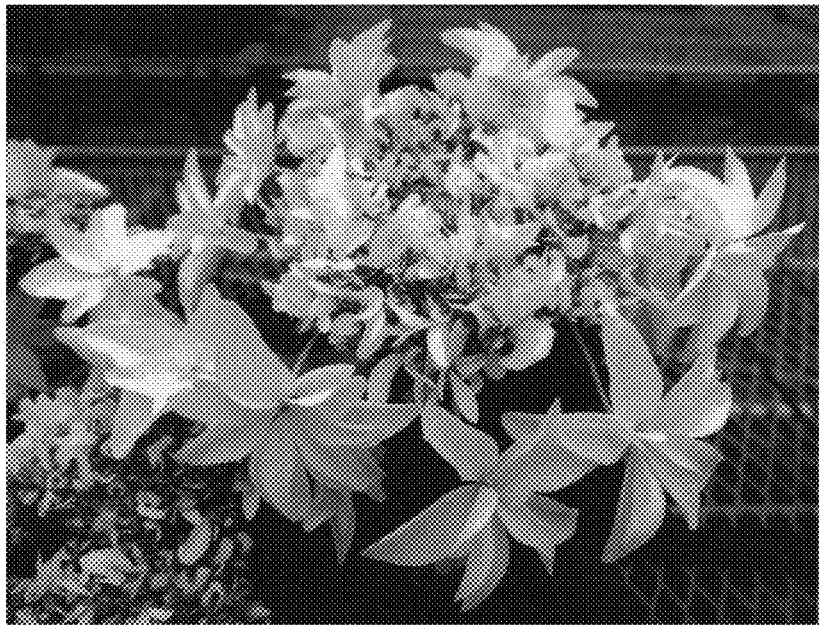

The photograph at the bottom of the sheet (FIG. 2) is a close-up view of typical inflorescences of 'CMT 010'.

DETAILED BOTANICAL DESCRIPTION

Plants used in the aforementioned photographs and in the following description were grown in containers in an outdoor nursery in Izumo-shi, Shimane, Japan and under cultural practices typical of commercial *Hydrangea* production. During the production of the plants, day temperatures ranged from about 15° C. to 25° C. Plants of the new *Hydrangea* were not pinched and were about twelve months from planting rooted young plants when the photographs were taken and about three months from planting rooted young plants when the description was taken. Plants of the new *Hydrangea* are not suitable to be treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* X *Hydrangea hybrida* 'CMT 010'.

Parentage:

*Female, or seed, parent.*—Proprietary selection of *Hydrangea macrophylla* X *Hydrangea hybrida* identified as code number Cmt005-014, not patented.

*Male, or pollen, parent.*—Proprietary selection of *Hydrangea macrophylla* X *Hydrangea hybrida* identified as code number Cmt005-014, not patented.

Propagation:

*Type cutting.*—By vegetative tip cuttings.

*Time to initiate roots, summer.*—About 30 days at temperatures about 15° C. to 25° C.

*Time to produce a rooted young plant, summer.*—About 90 days at temperatures about 15° C. to 25° C.

*Root description.*—Medium in thickness, fibrous; typically white to light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Relatively compact and uniformly mounded plant habit; upright and broadly outwardly spreading plant form; moderately vigorous growth habit and moderate growth rate.

*Plant height.*—About 35 cm.

*Plant diameter or area of spread.*—About 35 cm.

Lateral branch description:

*Branching habit.*—Freely branching habit with about four lateral branches per plant; pinching enhances lateral branch development.

*Length.*—About 10 cm to 15 cm.

*Diameter.*—About 5 mm.

*Internode length.*—About 5 cm to 6 cm.

*Strength.*—Moderately strong.

*Aspect.*—About 45° from vertical.

*Texture.*—Smooth, glabrous; fully developed, woody.

*Color, developing.*—Close to 187C; at the internodes, close to N144D.

*Color, fully developed.*—Close to 187B; at the internodes, close to 144A; woody, close to 199C.

*Lenticels.*—Density: Sparse. Length: About 2 mm. Width: About 0.5 mm. Color: Close to 187B.

Leaf description:

*Arrangement.*—Opposite, simple.

*Length.*—About 10.5 cm.

*Width.*—About 7.5 cm.

*Shape.*—Ovate.

*Apex.*—Acuminate.

*Base.*—Obtuse.

*Margin.*—Coarsely serrate.

*Texture and luster, upper and lower surfaces.*—Smooth, glabrous; matte.

*Venation pattern.*—Pinnate, reticulate.

*Color.*—Developing leaves, upper surface: Close to 143A. Developing leaves, lower surface: Close to 144A. Fully developed leaves, upper surface: Close to 139A; venation, to 145B. Fully developed leaves, lower surface: Close to 137C; venation, close to 145A.

*Petioles*.—Length: About 2 cm. Diameter: About 1.2 cm. Texture and luster, upper surface: Smooth, glabrous; matte. Texture and luster, lower surface: Smooth, glabrous; glossy. Color, upper surface: Close to 144B. Color, lower surface: Close to 144A.

Flower description:

*Flower type and habit*.—Showy rotate sterile flowers and conspicuous rotate fertile flowers arranged on intermediate lacecap-type terminal panicles; panicles semi-globular in shape; sterile and fertile flowers face mostly upright.

*Fragrance*.—None detected.

*Natural flowering season*.—In the garden, plants flower in the early summer in Japan; plants begin flowering about 65 days after planting rooted young plants.

*Flower longevity*.—Good postproduction longevity; fertile and sterile flowers last for about five weeks on the plant; flowers persistent.

*Quantity of flowers*.—Freely flowering habit; about eight sterile open flowers per panicle and about 450 fertile flowers per panicle.

*Panicle height*.—About 8 cm.

*Panicle diameter*.—About 21 cm.

*Fertile flower buds*.—Length: About 2 mm. Diameter: About 1 mm. Shape: Globose. Color: Close to 143B.

*Sterile flower buds*.—Length: About 5 mm. Diameter: About 2 mm. Shape: Elliptical. Color: Close to 145C.

*Fertile flower diameter*.—About 4 mm.

*Fertile flower depth* (*height*).—About 5 mm.

*Sterile flower diameter*.—About 7 cm.

*Sterile flower depth* (*height*).—About 1 cm.

*Petals, fertile flowers*.—Quantity and arrangement: Six in a single whorl. Length: About 1 cm. Width: About 5 mm. Shape: Lanceolate. Apex: Mucronate. Base: Acute. Margin: Entire. Texture and luster, upper and lower surfaces: Smooth, glabrous; matte. Color: When opening, upper surface: Close to 149C. When opening, lower surface: Close to 150B. Fully developed, upper surface: Close to 157D; color becoming closer to 145C with subsequent development. Fully developed, lower surface: Close to 155B; color becoming closer to 145C with subsequent development. Petals, sterile flowers: To date, petal development has not been observed on the sterile flowers.

*Sepals, fertile flowers*.—Quantity and arrangement: Five in a single whorl. Length: About 2 mm. Width: About 1 mm or less than 1 mm. Shape: Ovate. Apex: Acute. Base: Rounded. Margin: Entire. Texture and luster, upper and lower surfaces: Smooth, glabrous; matte. Color: When opening, upper and lower surfaces: Close to N144B. Fully developed, upper surface: Close to N144A; color becoming closer to 144C with subsequent development. Fully developed, lower surface: Close to N144B; color becoming closer to 144C with subsequent development.

*Sepals, sterile flowers*.—Quantity and arrangement: About eight or more in about one or two whorls. Length: About 3 cm. Width: About 1.5 cm. Shape: Lanceolate. Apex: Mucronate. Base: Obtuse. Margin: Entire. Texture and luster, upper and lower surfaces: Smooth, glabrous; matte. Color: When opening, upper and lower surfaces: Close to 150D. Fully developed, upper surface: Close to 155C; color becoming closer to 145C with subsequent development. Fully developed, lower surface: Close to 155C; color becoming closer to 145B with subsequent development.

*Pedicels, fertile flowers*.—Length: About 4 mm. Diameter: About 0.5 mm. Strength: Moderately strong. Aspect: Mostly upright. Texture and luster: Smooth, glabrous; matte. Color: Close to 143C.

*Pedicels, sterile flowers*.—Length: About 2 cm. Diameter: About 5 mm. Strength: Moderately strong. Aspect: Mostly upright. Texture and luster: Pubescent; matte. Color: Close to 157D.

*Reproductive organs, fertile flowers*.—Stamens: To date, stamen development has not been observed on fertile flowers of plants of the new *Hydrangea*. Pistils: Pistil quantity per flower: Three. Pistil length: About 1 mm or less than 1 mm. Stigma shape: Semi-globose. Stigma color: Close to 155B. Style length: About 1 mm or less than 1 mm. Style color: Close to 143C. Ovary color: Close to 143B.

*Reproductive organs, sterile flowers*.—Stamens: To date, stamen development has not been observed on fertile flowers of plants of the new *Hydrangea*. Pistils: Pistil quantity per flower: Three. Pistil length: About 1 mm. Stigma shape: Globose. Stigma color: Close to 145D. Style length: About 0.5 mm. Style color: Close to 143A. Ovary color: To date, ovary development has not been observed on sterile flowers of plants of the new *Hydrangea*.

*Seeds*.—To date, seed development has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to tolerate temperatures from −5° C. to 40° C.

It is claimed:

1. A new and distinct *Hydrangea* plant named 'CMT 010' as illustrated and described.

* * * * *